United States Patent [19]
Pahlck et al.

[11] Patent Number: 5,882,662
[45] Date of Patent: Mar. 16, 1999

[54] COSMETIC COMPOSITIONS CONTAINING SMECTITE GELS

[75] Inventors: Harold E. Pahlck, Waldwick; Leona Giat Fleissman, Ridgewood, both of N.J.

[73] Assignee: Avon Products, Inc., New York, N.Y.

[21] Appl. No.: 853,992

[22] Filed: May 9, 1997

[51] Int. Cl.⁶ ............................................. A61K 7/00
[52] U.S. Cl. .................... 424/401; 424/DIG. 5; 514/944
[58] Field of Search ............... 424/401, DIG. 5; 514/770, 944

[56] References Cited

U.S. PATENT DOCUMENTS

| | | | |
|---|---|---|---|
| 3,855,147 | 12/1974 | Granquist | 252/317 |
| 4,040,974 | 8/1977 | Wright et al. | 252/316 |
| 4,116,866 | 9/1978 | Finlayson | 252/316 |
| 4,275,222 | 6/1981 | Scala, Jr. | 560/103 |
| 4,425,244 | 1/1984 | House | 252/28 |
| 4,462,981 | 7/1984 | Smith | 424/27 |
| 4,550,035 | 10/1985 | Smith | 427/398.1 |
| 4,637,933 | 1/1987 | Arriban et al. | 424/131 |
| 4,659,571 | 4/1987 | Laba | 424/65 |
| 4,894,182 | 1/1990 | Cody et al. | 252/315.2 |
| 4,929,644 | 5/1990 | Guilbeaux | 514/642 |
| 5,015,469 | 5/1991 | Yoneyama et al. | 424/59 |
| 5,165,915 | 11/1992 | Tokubo et al. | 424/63 |
| 5,336,647 | 8/1994 | Nae et al. | 501/146 |
| 5,356,617 | 10/1994 | Schlossman | 424/63 |
| 5,376,604 | 12/1994 | Iwasaki et al. | 501/146 |
| 5,429,999 | 7/1995 | Nae et al. | 501/146 |
| 5,478,552 | 12/1995 | Hasegawa | 424/63 |
| 5,487,840 | 1/1996 | Yabe et al. | 252/62.51 |

*Primary Examiner*—Thurman K. Page
*Assistant Examiner*—James M. Spear
*Attorney, Agent, or Firm*—Ohlandt, Greeley, Ruggiero & Perle

[57] ABSTRACT

A cosmetic composition comprising a smectite clay and a lipophilic polar solvent. The smectite clay gels the polar solvent without addition of a polar activator. A method for the preparation of a smectite clay gel is also revealed.

25 Claims, No Drawings

COSMETIC COMPOSITIONS CONTAINING SMECTITE GELS

The present invention relates generally to cosmetic compositions containing smectite clay gels. More particularly, this invention relates to a cosmetic composition containing a synthetic smectite clay gelled with a polar solvent. The resulting composition or gel is used to bind and give structure to cosmetic compositions.

BACKGROUND OF THE INVENTION

Various binding and structuring agents are known for use in cosmetic compositions, such as lipsticks and eyeshadows. Traditionally, organic and inorganic waxes are used as binding and structuring agents in such compositions. However, many consumers dislike the inherently waxy feel and build-up of such wax-based cosmetics. Accordingly, a demand exists for non-wax binding and structuring agents.

A number of water-based gellants are in use in the cosmetic art as binding and structuring agents. These water-based gellants are primarily thickening agents, such as gums, added in limited amounts to aqueous carrier solutions. However, these thickening agents have limitations. For example, they must be incorporated into the composition under high temperature and high shear. In addition, clay based products such as the Bentone gels are also known for use as binding and structuring agents. These clay powders form gels in various oils. However, high shear must be applied to these clay-based gels during formulation, and separate polar activating agents such as propylene carbonate and other short chain polar compounds must be added to form the gels. Other clays, such as certain modified organophilic clays, are known to swell in and gel organic liquids without the addition of polar dispersion additives. However, these systems typically use such solvents as short chain alcohols, ketones or toluene, and require high energy shear to permit the gel to form.

Accordingly, there is a need for a cosmetic gel that can be used as a carrier to bind and give structure to the cosmetic composition, and that can replace part or all of the wax content of traditional cosmetic formulations.

SUMMARY OF THE INVENTION

Against the foregoing background, it is a primary object of the present invention to provide a cosmetic composition having a gelled carrier that is substantially wax-free or has a lower wax content than traditional cosmetics.

It is another object of the present invention to provide a cosmetic composition that can be formulated at low temperature and with the application of minimal shear.

It is yet another object of the present invention to provide a cosmetic composition that can be formulated as a liquid, poured or injected into a holder and subsequently heat set, to facilitate the packaging process.

To the accomplishment of the foregoing objects and advantages, the present invention, in brief summary, is a cosmetic composition comprising a smectite clay and a lipophilic polar solvent. The smectite clay gels the polar solvent without addition of a polar activator. A method for the preparation of a smectite clay gel is also revealed.

DESCRIPTION OF THE PREFERRED EMBODIMENTS

The present invention provides a unique cosmetic gel base comprising a clay, preferably a smectite clay, and a hydrocarbon-based lipophilic polar solvent. This cosmetic gel base is preferably a gel cosmetic, into which cosmetic agents such as colorants, emollients, and healing or treatment agents can be incorporated for delivery to the skin. Use of this cosmetic gel base allows the formation of a stick or cake cosmetic while eliminating or reducing the need for waxes or gums to bind or thicken the cosmetic composition. Finished products can also include soft gels and emulsions. In alternate embodiments, liquid and gel compositions can also be thickened with the gel of this invention. The smectite clay gel can act to improve yield value, or suspension of solids, within a liquid.

The preferred clay of the present invention is a smectite clay. More preferably, the clay is a synthetic smectite clay. Synthetic smectite clays are advantageous because they typically have a lower impurity content. However, any clay that has been cleaned to remove impurities can be used in the present invention.

The most preferred clay of the present invention is a synthetic smectite SAN clay distributed by Kobo Products Inc. and manufactured by Nikko Chemicals Co., Ltd. Kobo has disclosed the structure of its synthetic smectite clay, called lucentite SAN, as including 60.00 to 70.00 percent lithium magnesium sodium silicate ($Na_{0-0.33}$ ($Mg_{2.67}Li_{0.33}$) ($Si_4O_4$) ($OH$)$_2$) and 30.00 to 40.00 percent quaternium -18 ([$R_2N(CH_3)_2$], where R is $C_{16}$~$C_{18}$). Kobo has also stated that guaternium-18 is not reacted with lithium magnesium sodium silicate to form the lucentite SAN.

The present invention discloses the use of smectite SAN clay, swelled with a polar lipophilic hydrocarbon-based solvent, as a gel base or pomade for a cosmetic product. The cosmetic is preferably pigmented, but need not be. A pumpable product is produced that will set up once poured or injected into a mold. Moreover, the gelling agent/cosmetic base is chilled during formulation and is subsequently heat set to form a solidified product. This is contrary to typical cosmetic formulation practice in which the components are heated during mixing and the finished product is then cooled to set.

Gel stability is related to solvent polarity, with more highly polar solvents forming more stable gels. The smectite clay is preferably gelled with a polar lipophilic hydrocarbon-based solvent, more preferably a $C_6$ or higher polar solvent. The most preferred solvents are benzoate esters, such as $C_{12-15}$ alcohols benzoate (Finsolv TN), and salicylate esters. However, the solvent $C_{12-15}$ alcohol lactate is also preferred, since it also swells the synthetic smectite effectively.

The gelled smectite clay permits the formation of stick, cake or other solid or semi-solid cosmetics having no or limited wax content. The smectite clay gels provide stick integrity and lattice strength without the use of waxes. Moreover, liquid or other non-solid compositions can also be thickened with the gels of the present invention.

The smectite clay can be gelled with non-volatile lipophilic solvents. Of the non-volatile lipophilic solvents, organic solvents are preferred. Of these organic solvents, aromatic compounds are preferred, with esters being most preferred.

By varying the concentration of the smectite clay, a variety of product forms can result. For example, a liquid is formed at lower clay concentrations. At intermediate concentrations, a hot pour consistency is achieved. At higher concentrations, pomades and sticks can be formed.

These smectite clay gels have been found to have unique aesthetics. For example, when heat is applied to the clay/solvent mixture, the clay sets up instantaneously, forming a "standing wave." The stable gel that is created becomes sufficiently stiff to form peaks that do not flow back to their original position, so that the finished product has a smooth and creamy consistency. This unexpected result permits the gel that is formed to be used as a structural agent, and not just as a thickener. Depending on the content of pigments and powders, the finished product can also have a smooth powdery feel. Moreover, the gel and compositions containing the gel do not need to be compressed to form a cake or stick. Also, the finished product has an improved stability over time and over a wide range of temperatures. In addition, clearer, truer colors can be provided using the gel base of the present invention. Furthermore, the gel formed is unexpectedly clear or translucent, providing more versatility to the cosmetics formulator, including the option of producing clear or translucent finished products. Such clear products can be formulated, for example, when the smectite clays are cold mixed into organic oils containing aromatic ring structures, and the mixture is then heated. Furthermore, the finished product has good payoff, a smooth and creamy feel on application, and even delivery to the skin.

As discussed, the smectite gels of the present invention do not require high shear. Clay gels known in the art, such as Bentone gels, require the application of high shear to form the gels. Such high shear necessitates the addition of large quantities of mechanical energy to the system, as in a commercial homogenizer. On the other hand, the smectite gels of the present invention can be mixed by hand with a spatula, or with the commercial equivalent thereof. Sufficient force to thoroughly incorporate the pigments and other components into the solvent is required, but the use of high shear, as required by prior art clay gels, is not necessary.

Concerning the clear or translucent property of the finished product, the most preferred solvents, benzoate esters, form transparent gels when combined with the smectite clay and swelled with the application of heat. Finsolv TN ($C_{12}$–$C_{15}$ alcohols benzoate) is the most preferred ester for use in the compositions of the present invention. Pure $C_{12}$ and $C_{18}$ alcohols benzoate performed equivalently. When the smectite clay, preferably smectite SAN, is combined with octyl salicylate, a totally clear gel is formed. However, the gel strength is less than that of the Finsolv TN gel. This salicylate composition, after heating, reflects purple UV light. It appears that the smectite SAN solubilizes or disperses into this salicylate ester to provide the clear gel. Guerbet alcohols such as butyl octyl salicylate, butyl octyl benzoate and hexyl decyl benzoate also perform well as solvents.

Other preferred solvents include $C_{12}$–$C_{15}$ alcohol lactate (Ceraphyl 41 from ISP) and $C_{12}$–$C_{15}$ alcohol octanoate. Still other preferred solvents include phenyl trimethicone, Finsolv SB, Finsolv BOD, Finsolv PG-22, Surfadone LP300, Finsolv 116, Finsolv 137, Finsolv EMG20, alkyl 12–15 salicylate, tridecyl salicylate, isocetyl salicylate, laureth 2-benzoate, and phenylethylmethyl polydimethylsiloxane. Any aliphatic or aromatic polar solvent, organosilicone, ester, or compound or derivative thereof, can be used in the present invention.

Compositions of the present invention are also beneficial because they have superior high temperature stability. For example, they will not melt readily in hot climates or in hot car trunks. Furthermore, these compositions can be formulated to be wax free, and are resistant to or free of syneresis.

A preferred composition according to the present invention is formulated by the following steps:
1) mixing with minimal shear the synthetic smectite and the solvent at ambient to cold temperatures;
2) dispensing the mixture into a pan or other container;
3) applying heat to the mixture to swell and set the gel base.

The heat can be applied by radial, convectional, mechanical or electrical energy or by a combination thereof.

In the absence of other ingredients, it is preferred that the smectite clay be combined with the preferred Finsolv TN polar solvent at about 15% to about 85% by weight of the total weight of the composition. For example, a preferred two component stick can be made of about 20% by weight smectite clay and 80% by weight of Finsolv TN. A preferred multi-component pomade can be made of about 20% by weight smectite clay, about 20% by weight Finsolv TN, and about 60% adjunct ingredients such as pigments, film formers and preservatives. It is more preferred that the Finsolv TN be present at more than about 20% by weight of the total composition. However, the preferred amount of Finsolv TN can be varied depending on the effect other ingredients have on polarity. For example, phenyl trimethicone augments the polarity of the solvent, and accordingly less solvent is needed. Moreover, when other solvents are used in addition to or instead of Finsolv TN, the preferred amount will vary.

The resulting gel can be present at any weight percent of the total composition, depending on the desired function.

A preferred eyeshadow according to the present invention follows:

|  | Wt. % |
|---|---|
| Part A | 15 |
| Smectite SAN |  |
| Part B - Oil phase |  |
| Finsolv TN | 35 |
| Phenyl trimethicone | 3.7 |
| Film formers | 12.3 |
| Part C - Powders, etc. |  |
| Pearls and pigments | 22 |
| Powders | 11.5 |
| Methyl paraben | 0.3 |
| Propyl paraben | 0.2 |

In this preferred eyeshadow composition, it is most preferred that the powders contain a high concentration of platelet powders in relation to the concentration of particulate powders, to provide the desired cosmetic effect.

The foregoing composition was formulated according to the following procedure:
1. The oil phase ingredients were mixed.
2. The oil phase is placed in an ice bath or other cool environment at approximately 40° F.
3. After the oil phase has chilled, the smectite SAN is added.
4. The mixture is mixed until homogeneous, while maintaining the temperature.
5. The remaining ingredients are added and the mixture is mixed until homogeneous, maintained at 40° F. to 50° F.
6. The mixture is kept cool, preferably by storing in a refrigerator or freezer, until the batch is ready to be processed.

The batch is then packaged using the back injection molding process according to the following steps:
7. The batch or batches to be processed are placed into an ice bath.
8. Hoses conducting product from the back injection equipment are placed into the product containers.
9. The back injection process is run as usual, except there is no need for a vacuum to remove alcohol or other volatile components from the batch.
10. The filled pans are removed from the die and can be stored until needed.
11. The pan containing the product is heated to induce swelling of the smectite. The lattice of the gel is thus activated and the product is set and ready for use once the pan has cooled to ambient temperature.

The cosmetic compositions of the present invention are particularly suited for use with back injection equipment and process. This back injection process is commonly used in packaging cosmetic formulations. In this process, a solvent-based slurry of the cosmetic composition is injected through an aperture in the back, or base, of a cosmetic pan. The slurry then cools and solidifies in the pan to form the finished product. The cosmetic compositions of the present invention, however, can be slurried and injected at cool, ambient or heated temperature. They are pumpable when mechanical energy is applied, and set up when at rest. Thus, it is preferred to pump the product in a cool state (about 40° C. to about 50° C.) to prevent swelling until the product is in the final container. Moreover, no volatile solvent base is necessary. This, in turn, eliminates the need to evaporate off the alcohol or other volatile solvent.

The back injection molding process utilizes pans having holes through which the product is pumped. Each pan may have multiple holes, enabling more than one shade or product type to be filled into each pan without the need for double processing. Embossing and debossing is also feasible, to form raised or sunken surfaces on the finished product. This permits the creation of a wide variety of cosmetic effects. Dwell times, pressures and the use of a vacuum can affect the aesthetics of the surface of the finished product, and should be optimized for each formulation. The smectite clays of the present invention can be gelled and combined with a compatible volatile solvent, such as a polar volatile solvent, to provide a long-wearing product, which preferably also contains a cosmetic film former component. Additionally, the product can be swelled and set with the careful application of heat, making the process easier to control. The application of heat must be controlled (for example, the product can be heated in a closed container) to prevent evaporation of the volatile solvent when the volatile solvent is an integral part of the finished composition.

The invention having been thus described with particular reference to the preferred forms thereof, it will be obvious that various changes and modifications may be made therein without departing from the spirit and scope of the invention as defined in the appended claims.

What we claim is:

1. A cosmetic composition comprising a smectite clay and a lipophilic polar solvent, wherein said smectite clay gels said polar solvent without addition of a polar activator and without high shear.

2. The cosmetic composition of claim 1, wherein said smectite clay is synthetic.

3. A cosmetic composition comprising a smectite clay and a lipophilic polar solvent, wherein said smectite clay gels said polar solvent without addition of a polar activator and without high shear, and wherein said smectite clay is synthetic lucentite SAN.

4. A cosmetic composition comprising a smectite clay and a lipophilic polar solvent, wherein said smectite clay gels said polar solvent without addition of a polar activator and without high shear, and wherein said smectite clay includes lithium magnesium sodium silicate and quaternium-18.

5. The cosmetic composition of claim 4, wherein said lithium magnesium sodium silicate is present at about 60 to about 70 weight percent of the smectite clay, and said quaternium-18 is present at about 30 to about 40 weight percent of the smectite clay.

6. A cosmetic composition comprising:
   a smectite clay; and
   a lipophilic polar solvent selected from the group consisting of benzoate esters, salicylate esters, Guerbet alcohols, $C_{12}$–$C_{15}$ alcohol lactate, $C_{12}$–$C_{15}$ alcohol octanoate, phenyl trimethicone, Surfadone LP300, and phenylethylmethyl polydimethylsiloxane;
   wherein said smectite clay gels said polar solvent without addition of a polar activator and without high shear.

7. The cosmetic composition of claim 1, wherein said polar solvent is aromatic.

8. A method of forming a cosmetic composition, comprising:
   (a) mixing a smectite clay with a lipophilic polar solvent at a temperature of no more than about 40° F. to about 50° F. to form a clay/solvent mixture; and
   (b) heating said clay/solvent mixture to form a swelled gel.

9. A cosmetic composition comprising a smectite clay and a lipophilic polar solvent, wherein said smectite clay gels said polar solvent without addition of a polar activator and without high shear, and wherein said polar solvent is selected from the group consisting of benzoate esters, salicylate esters, $C_{12}$–$C_{15}$ alcohol lactate, and a combination thereof.

10. A cosmetic composition comprising a smectite clay and a lipophilic polar solvent, wherein said smectite clay gels said polar solvent without addition of a polar activator and without high shear, and wherein said composition is in a form selected from the group consisting of stick form and cake form.

11. The method of claim 8, wherein said composition is substantially clear.

12. A cosmetic composition comprising a smectite clay and a lipophilic polar solvent, wherein said smectite clay gels said polar solvent without addition of a polar activator and without high shear, and wherein said composition is substantially clear.

13. The cosmetic composition of claim 1, wherein said composition is translucent.

14. The method of of claim 8, wherein said composition is translucent.

15. The method of claim 8, wherein said clay/solvent mixture is kept cool before being heated.

16. The method of claim 8, further comprising a step of transferring said clay/solvent mixture into at least one cosmetic container, and wherein said clay/solvent mixture is heated in said at least one cosmetic container.

17. The method of claim 16, wherein said clay/solvent mixture is transferred into said at least one cosmetic container by a back injection process.

18. The method of claim 8, wherein said smectite clay is synthetic.

19. The method of claim 8, wherein said smectite clay is synthetic lucentite SAN.

20. The method of claim 8, wherein said smectite clay includes lithium magnesium sodium silicate and quaternium-18.

21. The method of claim 20, wherein said lithium magnesium sodium silicate is present at about 60 to about 70 weight percent of the smectite clay, and said quaternium-18 is present at about 30 to about 40 weight percent of the smectite clay.

22. The method of claim 8, wherein said polar solvent is organic.

23. The method of claim 22, wherein said polar solvent is selected from the group consisting of aromatic compounds, esters, silicones, and a combination thereof.

24. The method of claim 8, wherein said polar solvent is selected from the group consisting of benzoate esters, salicylate esters, $C_{12}$–$C_{15}$ alcohol lactate, and a combination thereof.

25. The cosmetic composition of claim 1, wherein said polar solvent is $C_6$ or higher.

* * * * *